United States Patent
Liao

(10) Patent No.: US 10,849,378 B2
(45) Date of Patent: Dec. 1, 2020

(54) COMPOSITION FOR MANUFACTURING GLOVES AND METHOD FOR MANUFACTURING GLOVES BY USING COMPOSITION

(71) Applicant: Ta-Chou Liao, New Taipei (TW)

(72) Inventor: Ta-Chou Liao, New Taipei (TW)

(73) Assignee: CHEM FIRST (TAIWAN) CO., LTD., New Taipei (TW)

( * ) Notice: Subject to any disclaimer, the term of this patent is extended or adjusted under 35 U.S.C. 154(b) by 312 days.

(21) Appl. No.: 15/626,176

(22) Filed: Jun. 19, 2017

(65) Prior Publication Data

US 2018/0014588 A1 Jan. 18, 2018

(30) Foreign Application Priority Data

Jul. 12, 2016 (TW) .............................. 105121856 A

(51) Int. Cl.
| | |
|---|---|
| *C08L 33/08* | (2006.01) |
| *C08K 3/22* | (2006.01) |
| *A41D 19/00* | (2006.01) |
| *C08J 5/02* | (2006.01) |
| *B05D 1/18* | (2006.01) |
| *C08K 3/36* | (2006.01) |
| *A61B 42/10* | (2016.01) |

(52) U.S. Cl.
CPC ..... *A41D 19/0082* (2013.01); *A41D 19/0062* (2013.01); *B05D 1/18* (2013.01); *C08J 5/02* (2013.01); *C08K 3/22* (2013.01); *C08K 3/36* (2013.01); *A61B 42/10* (2016.02); *C08J 2333/08* (2013.01); *C08K 2003/2227* (2013.01); *C08K 2003/2296* (2013.01)

(58) Field of Classification Search
CPC .............. C08K 3/36; C08K 2003/2227; C08K 2003/2296; C08L 33/08; C08L 13/02
See application file for complete search history.

(56) References Cited

U.S. PATENT DOCUMENTS

| | | | | |
|---|---|---|---|---|
| 7,345,111 | B2 * | 3/2008 | Ozawa | .................. C08F 220/18 |
| | | | | 524/800 |
| 9,808,039 | B2 * | 11/2017 | Enomoto | ........... A41D 19/0062 |
| 2008/0306201 | A1 * | 12/2008 | Beltrame | ................. C08K 3/22 |
| | | | | 524/432 |

OTHER PUBLICATIONS

Common White Pigments, downloaded from cameo.mfa.org on Aug. 27, 2019.*

* cited by examiner

*Primary Examiner* — Vu A Nguyen

(57) ABSTRACT

The present invention provides a composition used for manufacturing gloves comprising polyacrylate, which has glass transition temperature ($T_g$) under −20° C. The composition comprises characteristics of anti-sticking feature, alcohol resistance, anti-bacteria, anti-mildew, anti-UV, and without allergen. The gloves made by the composition can replace those made by traditional materials such as NBR, PVC, and so on. The composition used for gloves is able to apply to medical and electronics industries.

1 Claim, No Drawings

COMPOSITION FOR MANUFACTURING GLOVES AND METHOD FOR MANUFACTURING GLOVES BY USING COMPOSITION

CROSS-REFERENCE TO RELATED APPLICATION

This application claims the benefit of Taiwan Patent Application No. 105121856, filed on Jul. 12, 2016, in the Taiwan Intellectual Property Office of the R.O.C, the disclosure of which is incorporated herein in its entirety by reference.

FIELD OF INVENTION

The present invention relates to a composition. In particular, it relates to a glove made by the composition mainly applied in the field of electronics and medical industries.

BACKGROUND OF THE INVENTION

With the development of electronics and medical industries, the needs for gloves are more and more. Thus, the characteristics of desired gloves, such as alcohol resistance, film-forming feature, the strength of tear resistance, no allergens, anti-UV, anti-bacteria, anti-mildew, ventilation, and the like, are concentrated by users. In terms of electronics and medical industries, the development of gloves which have excellent aforementioned characteristics have long-felt need.

Traditional gloves are made by natural rubber, butyl rubber, and so on. Most gloves are copolymerized by two or more than two polymers. In conventional technology, an optional acrylate polymer can be blended with the urethane polymer dispersion or formed within the urethane polymer dispersion (typically referred to as hybrid polyurethane) to enhance alcohol resistance. Thus, acrylate polymer is necessary to added to achieve desired characteristics and functions in the electronics and medical industries.

As such, the electronics and medical industries are definitely in need of the gloves with the characteristics of alcohol resistance, softness, anti-sticking feature, and smoothness. However, in aforementioned related arts, in addition to using acrylate polymer, another material is also used, such as polyurethane, polyvinyl chloride (PVC), acrylonitrile-butadiene rubber polymer, styrene-butadiene rubber polymer, adhesives, and the like. Some materials, such as plasticizer, added in the gloves may be harmful to our human body. In addition, nitrile butadiene rubber or waterborne polyurethane is also used, wherein waterborne polyurethane is good at film-forming feature, elasticity, toughness, and compensation with the disadvantage of anti-sticking feature, but is bad at heat resistance, alcohol resistance, resistance to solvent with strong polarity, resistance to strong acid and alkali medium, and so on.

The above information disclosed in this section is only for enhancement of understanding of the background of the described technology and therefore it may contain information that does not form the prior art that is already known to a person of ordinary skill in the art.

SUMMARY OF THE INVENTION

The present invention offers a glove simply made by polyacrylate. The product has advantages of good softness, anti-sticking feature, and tensile force, and is able to replace traditional gloves made by waterborne polyurethane, natural rubbers, PVC, or the like. It meets the needs of electronics industry and surgical operation.

The present invention provides a composition used for manufacturing gloves, which is simply made by polyacrylate. The gloves having characteristics of alcohol resistance, film-forming feature, the strength of tear resistance, no allergens, anti-UV, anti-mildew, anti-bacterial feature, ventilation, biodegradation with environment-friendly feature, and the like. The process is simple and meets the needs of electronics industry and surgical operation.

The present invention provides a composition used for manufacturing gloves, comprising polyacrylate having glass transition temperature ($T_g$) $-20°$ C.$\sim$$-70°$ C.; and an additive, wherein the weight of polyacrylate is ranged 90 wt %~96 wt % based on the total weight of composition, and the additive as a remainder to make up 100 wt %.

In the embodiment of the present invention, the polyacrylate is polyethylacrylate, polybutylacrylate, polyisooctyl acrylate, or combination thereof.

In the embodiment of the present invention, based on the total weight of composition, the additive further comprises 1.4 wt %~3.5 wt % sodium dodecyl sulfate as an emulsifier used in emulsion polymerization reaction.

In the embodiment of the present invention, based on the total weight of composition, the additive further comprises 1.6 wt %~4 wt % itaconic acid as an internal crosslinking agent.

In the embodiment of the present invention, based on the total weight of composition, the additive further comprises 1 wt %~2.5 wt % cohesion enhancer as increasing cohesive force of polyacrylate.

Wherein the cohesion enhancer is aluminium oxide, silicon dioxide, zinc oxide, or combination thereof.

The present invention also provides a method of manufacturing gloves, comprising (a) providing an emulsion of aforementioned composition; (b) immersing a mold of gloves into the solution of aforementioned composition; and (c) drying the mold of gloves to obtain the gloves.

Wherein the mold of gloves is put into an oven with $70°$ C. before the aforementioned step (c).

Wherein the mold of gloves are dried under $120°$ C.

Many of the attendant features and advantages of the present invention will become better understood with reference to the following detailed description considered in connection with the accompanying drawings.

DETAILED DESCRIPTION OF THE PREFERRED EMBODIMENTS

Reference will now be made in detail to the exemplary embodiments of the present invention, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this invention will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way.

For convenience, certain terms employed in the specification, examples and appended claims are collected here. Unless defined otherwise, all technical and scientific terms used herein have the same meaning as commonly understood by one of the ordinary skill in the art to which this invention belongs.

Various embodiments will now be described more fully with reference to the accompanying drawings, in which illustrative embodiments are shown. The inventive concept, however, may be embodied in various different forms, and should not be construed as being limited only to the illustrated embodiments. Rather, these embodiments are provided as examples, to convey the inventive concept to one skilled in the art. Accordingly, known processes, elements, and techniques are not described with respect to some of the embodiments.

The following definition is applied in all disclosure of the present invention. The weight percentage of all polymers, gels, and other materials is represented by dry weight basis. The term "polymer" means homopolymer and copolymer. The term "polymerization unit" means a polymerized molecule, such as polyacrylate, which includes polymerization unit or molecule of polyacrylate.

The singular forms "a", "and", and "the" are used herein to include plural referents unless the context clearly dictates otherwise.

In addition, "polyacrylate" is a generic term used to describe polymers including oligomers (e.g., prepolymers) which contain the acrylate, regardless of how they are made. As well known, these polyacrylates can contain additional groups such as methyl, isooctyl, etc., in addition to acrylate.

"Wt. %" means the number of parts by weight of monomer per 100 parts by weight of polymer, or the number of parts by weight of ingredient per 100 parts by weight of composition or material of which the ingredient forms a part. In the present invention, the oxidant, antioxidant, reducing agent, initiator, stabilizer, or the like is only used to initiate chemical reaction, redox reaction, or stabilize the reaction, but not used for raw material of composition.

"Aqueous medium" means a composition containing a substantial amount of water, e.g., at least 40 or 80 wt. % water based on the aqueous medium of the dispersion. It may contain other ingredients as well.

"Latex" refers to a dispersion with polymer particles dispersed in aqueous medium, and the diameter of particles is usually ranged $10^{-6} \sim 10^{-7}$ m.

"Emulsion polymerization" refers to a polymerization reaction initiated by radical groups, where water is used as continuous phase (or carrier), and a monomer is used as dispersed phase.

The "final polyacrylate product" refers to the form of the polyacrylate in the aqueous dispersion product of this invention. Where the polyacrylate prepolymer is optionally chain extended, the final polyacrylate product is this chain extended polymer. Where the polyacrylate prepolymer is not chain extended, the final polyacrylate product is the prepolymer itself.

"Substantially absence of water" refers to compositions formed without the intentional addition of any significant amount of water, e.g., about 2 wt. % or less or so.

The following descriptions are provided to elucidate the process of preparing a composition used for manufacturing gloves and to aid it of skilled in the art in practicing this invention. These Examples are merely exemplary embodiments and in no way to be considered to limit the scope of the invention in any manner.

The present invention provides a composition used for manufacturing gloves, which is prepared in conventional technology. Thus, the method and formula of manufacturing gloves are only described as follows.

The present invention provides a composition prepared by emulsion polymerization reaction, the formula mainly comprises: water, monomers, initiators, emulsifiers, and other auxiliaries. Based on the total weight of formula, the weight of water is ranged 40 wt %~80 wt %, preferably 65 wt %, the weight of monomers is ranged 20 wt %~60 wt %, preferably 35 wt %; the concentration of initiators is around 0.1~0.3 ppm, the concentration of emulsifiers is around 1~5 ppm, and other auxiliaries are optionally added.

In the present invention, it should be noticed that the pH value, category of ions, and ion contents of the aqueous medium used in emulsion polymerization reaction are the most important, and those characteristics significantly influence the conversion rate and activity of the polymerization reaction. Where water content depends on solid content.

In the embodiment of the present invention, in order to meet different needs, more than two acrylate monomers are employed to achieve copolymerization reaction. Monomer choices can be considered as follows: (1) glass transition temperature ($T_g$) of polymer: as for polymer, theoretical $T_g$ is: $1/T_g = W_1/T_{g1} + W_2/T_{g2} + \ldots W_n/T_{gn}$ since every monomer has different $T_g$; (2) the interaction between monomers; (3) certain monomers have special functional groups, which provide internal crosslinking reaction for monomers, such that products have better characteristics. Furthermore, in order to make products softness and anti-stickiness, special internal crosslinking monomers and redox agents are employed to proceed polymerization reaction.

In the embodiment of the present invention, free radical initiators used in emulsion polymerization reaction have two types: (1) thermos decomposition type: peroxide, such as $K_2S_2O_4$; (2) redox type: oxidant or reducing agent, such as KPS+SBS, sodium persulfate, potassium persulfate, sodium metabisulfite, and so on. The aspect of initiators in the present invention is just exemplary, but not limited thereto. Normal initiators can be used in the present invention and depend on reaction temperature. The influence of category and dosage of initiator on polymerization reaction including: (1) conversation rate of polymerization reaction; (2) molecule weight of polymers; (3) particle number and size of polymers.

In the embodiment of the present invention, emulsifiers can be used before polymerization reaction. The emulsifiers form as micells, which enhance acrylate monomers to dissolve in aqueous medium, and then the polymerization reaction is proceeded. After completing polymerization reaction, micells further enhances stability of particles (mechanical stability and chemical stability). The structure basically includes two parts: (1) lipophilic groups; and (2) hydrophilic groups. There are four categories: (1) anionic type: when this type of surfactants dissolve in water, they dissociate into anionic surfactants; (2) cationic type: which contraries to anionic type, when this type of surfactants dissolve in water, they dissociate into cationic surfactants, such as sodium dodecyl sulfate (SDS) $CH_3(CH_2)_{11}OSO_3^-Na^+$, which is the main ingredient in toothpaste, sodium dodecyl benzene sulfonate $R-C_6H_4SO_3^-Na^+$, which is the general formula of detergent, and alkyl sodium carbonate $R-CO_2^-Na^+$, this series of carbonate is commonly known as soap; (3) zwitterionic type: this type of surfactants have characteristics of anionic type and cationic type, such as $CH_3(CH_2)_{13}N^+H_2CH_2CH_2SO_3^-Na^+$; (4) nonionic type: the hydrophilic group of this type of molecule does not dissociate, but the polar functional group, such as hydroxyl group (—OH), ether group (—O—), imine group (—NH—), and so on, can interact with water molecule to produce hydrogen bond. For example, $CH_3(CH_2)_{11}(OCH_2CH_2)_8OH$. Many surfactants aggregate into micells. In water solution, the hydrophilic group of the surfactant in micells outwardly hydrolyzes with water molecules, and the hydrophobic chain is enclosed to reduce the contact area between water molecules and the hydrophobic chain. Although micells are usually spherical shape, actual size and shape change with concentration and temperature. They can change to cylindrical or layer structure.

In the embodiment of the present invention, auxiliaries could be added according to needs, such as bond transfer agent, buffer agent, film-making agent, preservative, eliminator, neutralizer, filler, and so on.

After preparing materials, emulsion polymerization reaction is proceeded. The steps are described as follows.

First step: particle nucleation mechanism, which includes micellar nucleation, homogeneous nucleation, coagulative nucleation, monomer droplet nucleation, and so on. When all particles form completely and no particle is produced, first step is finished. In this step, particle number, particle size, and conversion rate gradually increase.

Second step: particle growth mechanism. In this step, the particle number maintains constant value, and overall conversion rate also maintain constant value. When the monomers in emulsion droplets are used up, the process gets into the third step.

Third step: particle formation mechanism. In this step, emulsified monomers disappear, and there are no monomers from outside in the growth particles. The polymerization rate depends on diffusion-controlled polymerization.

After polymerization reaction, a composition used for manufacturing gloves can be obtained. Thus, the present invention provides a composition used for manufacturing gloves, which is mainly applied in electronics, chemical, and medical industry.

The present invention provides a composition used for manufacturing gloves, comprising polyacrylate having glass transition temperature ($T_g$) under −20° C., preferably −20° C.~−70° C., more preferably under −70° C.; and an additive, wherein the weight of polyacrylate is ranged 90 wt %~96 wt %, preferably 94 wt %, based on the total weight of composition, and the additive as a remainder to make up 100 wt %. It should be noted that controlling the weight percentage of polyacylate makes products softness, anti-stickness, and toughness. However, if acrylate monomer is added too much, it's not good for polymerization reaction; on the contrary, if acrylate monomer is added too few, the thickness of products would be too thin. As such, the weight percentage of polyacrylate is controlled precisely and critically, so as to achieve the best effect.

In the embodiment of the present invention, in order to make products have softness feature, the acrylate having low $T_g$ value is employed in the present invention. Preferably, the acrylate is ethyl acrylate, butyl acrylate, isooctyl acrylate, or combination thereof, where the $T_g$ of ethyl acrylate is −23° C., the $T_g$ of butyl acrylate is −42° C., and the $T_g$ of isooctyl acrylate achieves −70° C.

Preferably, based on the total weight of composition, the additive further comprises 1.4 wt %~3.5 wt % sodium dodecyl sulfate as an emulsifier used in emulsion polymerization reaction.

Preferably, based on the total weight of composition, the additive further comprises 1.6 wt %~4 wt % itaconic acid as an internal crosslinking agent.

Preferably, based on the total weight of composition, the additive further comprises 1 wt %~2.5 wt % cohesion enhancer as increasing cohesive force of polyacrylate, wherein the cohesion enhancer is aluminium oxide, silicon dioxide, zinc oxide, or combination thereof.

Preferably, the gloves, which are final product of the present invention, are substantially absence of water.

Preferably, appropriate internal crosslinking agents can be added in the process, so that the products obtain tear resistance feature.

In addition, itaconic acid is used to replace traditional N-methylolacrylamide and acrylamide to be the internal crosslinking agent in the present invention, and makes the products without formaldehyde.

In addition, the present invention uses nanosized powder of aluminium oxide, zinc oxide, silicon dioxide, or combination thereof as the cohesion enhancer to make the products have characteristics of film-forming feature, the strength of tear resistance, no allergens, anti-UV, anti-mildew, anti-bacteria etc.

EXAMPLE

The following descriptions represent merely the exemplary embodiment of the present invention, without any intention to limit the scope of the present disclosure thereto. Various equivalent changes, alternations or modifications, based on the claims of present invention are all consequently viewed as being embraced by the scope of the present invention.

Sodium dodecyl sulfate (K-12) 4.5 kg is used to dissolve in water 400 kg, and this solution is poured into a polymerization tank to heat until 55° C. At that time, ethyl acrylate 18 kg and itaconic acid 0.3 kg are added into the polymerization tank respectively, and stir under 63° C. In this embodiment, sodium dodecyl sulfate is used as the emulsifier used in emulsion polymerization reaction.

Wherein ethyl acrylate can be replaced by butyl acrylate, isooctyl acrylate, or combination of those three acrylate.

Sodium persulfate 1.13 kg as the initiator (potassium persulfate or ammonium persulfate can also be used), ferrous sulfate 0.000625 kg as the stabilizer, and sodium metabisulfite 0.019 kg as the reducing agent are respectively poured into water 80 kg, and then this solution is poured into the polymerization tank after emulsion in the polymerization tank becomes blue.

Ethyl acrylate 342 kg (or butyl acrylate, isooctyl acrylate, or those three combination), itaconic acid 5.7 kg, and sodium metabisulfite 0.361 kg are respectively added into the polymerization tank, and the polymerization tank is stirred until the reaction completes.

In addition, tert-butyl hydroperoxide 0.4 kg as the oxidant is added into water 6 kg, ascorbic acid 0.3 kg as the antioxidant is added into water 30 kg, and then those two solutions are poured into the polymerization tank.

The polymerization tank is heated to 68~70° C., and the polymerization reaction is proceeded 30 minutes. Then the temperature is reduced to 40~45° C.

Aluminium oxide, silicon dioxide, zinc oxide, or combination thereof 3.5 kg is added into water 64 kg, and the solution is stirred and poured into the polymerization tank. The emulsion of polymerization tank can be used for manufacturing gloves after it is cured 40~60 minutes. Based on the total weight of emulsion, the solid content of polyacrylate is ranged 20 wt %~60 wt %. It should be noted that aluminium oxide, silicon dioxide, zinc oxide, or combination thereof is the cohesion enhancer, and its particle size is nanosized. The average diameter of cohesion enhancer is around 1~100 nm, preferably 30~70 nm. The advantage of nanoparticle makes $T_g$ of polyacrylate lower, and increases function of toughness, strength of tear resistance, anti-mildew, and anti-bacterial feature.

The solid weight of final product in this embodiment is 385.21 kg.

Titanium dioxide may be considered (not necessary) to be added into the final polyacrylate emulsion, but it depends on needs. The effect of adding titanium dioxide makes the final products have smoothness and anti-sticking feature. However, if titanium dioxide is added too much, the characteristics of opacity would increase; if titanium dioxide is added too less, the anti-sticking and film-making features would be bad. The person having ordinary skills in the art may depend on their needs to control the quantity of titanium dioxide they need or if titanium dioxide is added.

The wetting agent and leveling agent may also be considered (not necessary) to add into the final polyacrylate emulsion, and it depends on needs. The person having ordinary skills in the art may depend on their needs to control the quantity of wetting agent and leveling agent they need or if wetting agent and leveling agent are added. The wetting agent is able to increase operation feature of the gloves made by polyacrylate in the present invention, and the leveling agent is able to increase leveling feature.

When manufacturing gloves, the mold of gloves is put to oven to heat to around 70° C., and then the mold of gloves is immersed into the polyacrylate emulsion.

After that, the mold of gloves is put into oven 120° C. to heat for 1 minute, and is crimped by a crimping tool. The mold of gloves is put into oven 120° C. to dry. After that, the mold of gloves is taken out and a slipping agent including an emulsified wax and silicon dioxide is added on that, and then the mold of gloves is dried and demolded to obtain the gloves.

Result

After obtaining the gloves, the gloves are sent to test by a cupping machine, and the results are described and analyzed in Table 1 as follows.

TABLE 1

| Performance | Glove 1 (Commercial gloves) | Glove 2 (Gloves of the present invention) |
| --- | --- | --- |
| Minimum of breaking tenacity before aging (N; Newton) | 12 | 14 |
| Minimum percentage of breaking elongation before aging (%) | 700 | 720 |
| Maximum of 300% elongation loading force after aging (N) | 2 | 2.2 |
| Minimum of breaking tenacity after aging (N) | 9.5 | 12.5 |
| Minimum percentage of breaking elongation after aging (%) | 550 | 650 |

From table 1, compared with commercial gloves, gloves of the present invention enhance many physical features. For example, minimum of breaking tenacity before aging tested for Glove 2 increase 2N (at least 16%) compared with that tested for Glove 1; minimum percentage of breaking elongation before aging tested for Glove 2 increase at least 20% compared with that tested for Glove 1; maximum of 300% elongation loading force after aging tested for Glove 2 increase 0.2N (at least 10%) compared with that tested for Glove 1; especially minimum of breaking tenacity after aging tested for Glove 2 increase 3N (at least 31%) compared with that tested for Glove 1; minimum percentage of breaking elongation after aging tested for Glove 2 increase at least 100% compared with that tested for Glove 1. As such, the gloves made by the present invention do not merely have antibacterial and anti-mildew function, but also have excellent anti-sticking, elasticity, and toughness features. Thus, the gloves made by the present invention are good enough to replace commercial electronics and medical gloves.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations or modifications, such as polymers which have similar characteristics with polyacrylate, to the disclosed embodiments without departing from the spirit or scope of this invention.

What is claimed is:

1. A mixture for manufacturing gloves, consisting of a polyacrylate having a glass transition temperature ($T_g$) of −20° C. to −70° C. and an additive, wherein the weight of the polyacrylate is from 90 wt % to 96 wt %, based on the total weight of the mixture, and the additive as a remainder to make up 100 wt %, and wherein the additive comprises 1 wt % to 2.5 wt %, based on the total weight of the mixture, of a cohesion enhancer, which is a nanosized powder of zinc oxide.

* * * * *